US010858643B2

(12) United States Patent
Dobrinsky et al.

(10) Patent No.: US 10,858,643 B2
(45) Date of Patent: Dec. 8, 2020

(54) VACCINE PREPARATION USING ULTRAVIOLET RADIATION

(71) Applicant: Sensor Electronic Technology, Inc., Columbia, SC (US)

(72) Inventors: Alexander Dobrinsky, Loudonville, NY (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 609 days.

(21) Appl. No.: 15/338,913

(22) Filed: Oct. 31, 2016

(65) Prior Publication Data

US 2017/0121701 A1    May 4, 2017

Related U.S. Application Data

(60) Provisional application No. 62/248,435, filed on Oct. 30, 2015.

(51) Int. Cl.
| | | |
|---|---|---|
| *C12N 13/00* | (2006.01) | |
| *C12N 7/00* | (2006.01) | |
| *C12N 1/36* | (2006.01) | |
| *A61K 39/00* | (2006.01) | |
| *A61L 2/00* | (2006.01) | |

(52) U.S. Cl.
CPC .............. *C12N 13/00* (2013.01); *A61K 39/00* (2013.01); *A61L 2/0047* (2013.01); *C12N 1/36* (2013.01); *C12N 7/00* (2013.01); *A61K 2039/521* (2013.01); *A61K 2039/5252* (2013.01)

(58) Field of Classification Search
CPC ........... C12N 13/00; C12N 7/00; A61K 39/00
See application file for complete search history.

(56) References Cited

U.S. PATENT DOCUMENTS

| | | |
|---|---|---|
| 4,612,007 A | 9/1986 | Delson |
| 4,683,889 A | 8/1987 | Delson |
| 5,342,752 A | 8/1994 | Platz et al. |
| 5,798,238 A | 8/1998 | Goodrich, Jr. et al. |
| 6,258,577 B1 | 7/2001 | Goodrich, Jr. et al. |
| 6,268,120 B1 | 7/2001 | Platz et al. |
| 6,277,337 B1 | 8/2001 | Goodrich, Jr. et al. |
| 8,759,092 B2 | 6/2014 | Goodrich |
| 2005/0101025 A1* | 5/2005 | Ho .................. B01L 3/0275 436/86 |
| 2011/0009608 A1* | 1/2011 | Kim .................. C12N 15/1013 536/25.41 |
| 2014/0060096 A1* | 3/2014 | Shur .................. A61L 2/10 62/132 |
| 2014/0202962 A1* | 7/2014 | Bilenko .................. C02F 1/325 210/748.11 |
| 2015/0069265 A1* | 3/2015 | Smetona .................. A61L 2/10 250/455.11 |
| 2017/0095582 A1 | 4/2017 | Shur et al. |

* cited by examiner

*Primary Examiner* — Taeyoon Kim
*Assistant Examiner* — Tiffany M Gough
(74) *Attorney, Agent, or Firm* — LaBatt, LLC

(57) ABSTRACT

An approach for preparing a vaccine using ultraviolet radiation is described. Aspects of this approach involve multiple iterations of inactivation of the vaccine using an ultraviolet radiation source at a set of different wavelengths and dosages. A recognition test of the vaccine using the set of different wavelengths and dosages is performed after the multiple iterations of inactivation. A controller compares results from the inactivation test and the recognition test to determine an area of acceptable radiation dosages and wavelengths generated from the ultraviolet radiation source that irradiate the live organisms without affecting efficacy and safety of the vaccine. The area of acceptable ultraviolet radiation dosages and wavelengths is representative of a difference between an ultraviolet radiation dosage that is required for inactivation and an ultraviolet radiation dosage that leads to a loss of recognition.

20 Claims, 10 Drawing Sheets

- Culture Radiation Test (106) → Recognition Test (108) → Save Radiation Patterns Leading To Recognition (110) | R1 | R2 | R3 | R4 |

FIG. 13

Wavelength (250nm–300nm) vs Energy Dose

- 112
- 114: Dose sufficiently small such that the organism is recognized by Immune system
- 116: Dose is large such that the organism is not-recognized by Immune system

VACCINE PREPARATION USING ULTRAVIOLET RADIATION

REFERENCE TO RELATED APPLICATIONS

The present patent application claims the benefit of U.S. Provisional Application No. 62/248,435, which was filed on 30 Oct. 2015, and which is hereby incorporated by reference.

TECHNICAL FIELD

The present invention relates generally to the preparation of a vaccine, and more particularly, to using ultraviolet radiation to inactivate an antigen in a vaccine at a wavelength of light and dosage of ultraviolet radiation that is effective in generating an immunogenic response to the antigen.

BACKGROUND ART

In the process of developing immunity to an infectious agent, B cells of the body produce substances known as antibodies that act against the specific infectious agent and create a "memory" of this experience that can be called upon for protection when exposed to the same infectious agent again months or years later. The next time the person encounters this particular infectious agent, the circulating antibodies quickly recognize it and enable it to be eliminated from the body by other immune cells before signs of disease develop. It is estimated that antibodies which can recognize over 10,000 different antigens or foreign (non-self) infectious agents are circulating in the blood stream.

A vaccine works in a similar way in that it produces an immunogenic response. However, instead of initially suffering the natural infection and risking illness in order to develop this protective immunity, vaccines create a similar protective immunity without exposing the body to the disease. Development of vaccines against both bacterial and viral diseases has been one of the major accomplishments in medicine over the past century. While effective vaccines have been developed for a large number of diseases, the need for development of safe and effective vaccines for a number of additional diseases remains.

Several basic strategies are used to make vaccines. One strategy is directed toward preventing viral diseases by weakening or attenuating a virus so that the virus reproduces very poorly once inside the body. Measles, mumps, rubella (German measles) and chickenpox (varicella) vaccines are made this way. Whereas natural viruses usually cause disease by reproducing themselves many thousands of times, weakened vaccine viruses reproduce themselves approximately 20 times. Such a low rate of replication is generally not enough to cause disease. Although the preparation of live, attenuated infectious agents as vaccines will often provide improved immunologic reactivity, such methods do increase the risk that the vaccine itself will be the cause of infection, and that the attenuated organism will propagate and provide a reservoir for future infection. One or two doses of live "weakened" viruses may provide immunity that is life long; however, such vaccines cannot be given to people with weakened immune systems.

Another way to make viral vaccines is to inactivate the virus. By this method, viruses are completely inactivated or killed using a chemical. Killing the virus makes the virus unable to replicate in a body and cause disease. Polio, hepatitis A, influenza and rabies vaccines are made this way. The use of inactivated or killed bacterial or viral agents as a vaccine used to induce an immunogenic response, although generally safe, will not always be effective if the immunogenic characteristics of the agent are altered. An inactive virus can be given to people with weakened immune systems, but must be given multiple times to achieve immunity.

Vaccines may also be made using parts of the virus. With this strategy, a portion of the virus is removed and used as a vaccine. The body is able to recognize the whole virus based on initial exposure to a portion of the virus. The hepatitis B vaccine for example, is composed of a protein that resides on the surface of the hepatitis B virus.

Vaccines are also made to help combat diseases caused by bacteria. Several bacterial vaccines are made by taking the toxins produced by bacteria and inactivating them using chemicals. By inactivating the toxins, the bacteria no longer causes disease. Diphtheria, tetanus and pertussis vaccines are made this way. Another strategy to make bacterial vaccines is to use part of the sugar coating (or polysaccharide) of the bacteria to induce the immunogenic response. Protection against certain bacteria are based on responsive immunity to this sugar coating.

Thus, one must generally choose between improved effectiveness or greater degree of safety when selecting between the inactivation and attenuation techniques for vaccine preparation. The choice is particularly difficult when the infectious agent is resistant to inactivation and requires highly rigorous inactivation conditions which are likely to degrade the antigenic characteristics which help to induce an immune response and provide subsequent immunity. In addition to the dead or weakened infectious agent, vaccines usually contain sterile water or saline. Some vaccines are prepared with a preservative or antibiotic to prevent bacterial growth. Vaccines may also be prepared with stabilizers to help the vaccine maintain its effectiveness during storage. Other components may include an adjuvant which helps stimulate the production of antibodies against the vaccine to make it more effective.

Methods to prepare vaccines today involve treating samples with glutaraldehyde or formaldehyde to fix or cross-link the cells or infectious particles. Such treatments generally involve denaturation of the native forms of the infectious particles. A disadvantage to this approach is that the protein coats of the infectious particles are damaged by this process, and thus may not be recognized by the immune system.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to the inactivation of infectious agents such as viruses or bacteria through the use of ultraviolet radiation for the purpose of developing a vaccine that stimulates antibody production that confers immunity to a particular disease. In one embodiment, an ultraviolet radiation source such as a light emitting diode (LED) lamp having individual LED sources each configured to irradiate at a specific wavelength selected from a range extending from 250 nm to 360 nm can be used in the inactivation of live samples of the viruses or bacteria. In one embodiment, the individual LED sources can be arranged in a matrix array. In another embodiment, the individual LED sources can be arranged on a LED source holder located over the samples and oriented to irradiate the samples in a desired manner. The LED source holder can take the form of a variety of shapes such as for example, a ring shape or a rectangular shape.

Optical elements can be used in conjunction with the ultraviolet radiation source to facilitate the inactivation process. For example, at least one diffusive element can be used to increase the efficiency of the irradiation to the samples of the viruses or bacteria. In one embodiment, a first diffusive element can be placed over the samples and a second diffusive element can be placed underneath the samples, while the ultraviolet radiation source can be located between the first diffusive element and the second diffusive element. In an embodiment in which the ultraviolet radiation source is a LED lamp, the individual LED sources can be oriented on the LED source holder such that the sources direct ultraviolet radiation towards the first diffusive element, which directs the ultraviolet radiation toward the samples placed on the second diffusive element. In this embodiment, the first diffusive element and the second diffusive element can include a highly diffusively reflective material and a diffusively transparent material, respectively, while the LED source holder can include an ultraviolet transparent material. Other optical elements that can be used to ensure diffusive illumination include mirrors, diffusive films, and/or the like that increase scattering of the ultraviolet light.

Motion rails system can be used with the various ultraviolet radiation source configurations to effectuate irradiation of the samples in the inactivation and recognitions phases of the development of the vaccine. In one embodiment, a first linear motion rail and a second linear motion rail operate in conjunction to move the ultraviolet radiation source in a predetermined direction with respect to the samples. In particular, the first linear motion rail can be configured to move the ultraviolet radiation source in a horizontal direction over the samples, while the second linear motion rail can be configured to move the ultraviolet radiation source in a vertical direction over the samples. In another embodiment, a two-dimensional rail system having an x-axis motion rail and a y-axis motion rail can operate in conjunction to move the samples in two-dimensional movements that include x-axis directional movements and y-axis directional movements with respect to the ultraviolet radiation source.

A controller can be configured to control the irradiation of the live samples by the ultraviolet radiation source during the development and preparation of the vaccine. In one embodiment, the controller can direct the ultraviolet radiation source to perform an inactivation test of the live samples using ultraviolet radiation irradiated at a plurality of different wavelengths and a plurality of different dosages of ultraviolet radiation. The controller can compare results from the inactivation test against results obtained from a recognition test in which samples of the vaccine irradiated at the plurality of different wavelengths and the plurality of different dosages of ultraviolet radiation are evaluated for an immunogenic response to an antigen with an antibody that acts against the antigen. The controller can determine an area of acceptable radiation dosages and wavelengths generated from the ultraviolet radiation source without affecting the efficacy in obtaining the immunogenic response to the antigen and safety of the vaccine. In one embodiment, the area of acceptable ultraviolet radiation dosages and wavelengths is representative of a difference between an ultraviolet radiation dosage that is required for inactivation and an ultraviolet radiation dosage that fails to obtain the immunogenic response.

In one embodiment, a plurality of vaccine delivery channels can be configured to deliver a predetermined amount of vaccine to the samples. In particular, each delivery channel can deliver a predetermined amount of vaccine to one of the samples. In one embodiment, each vaccine delivery channel can include a set of the LED sources that are configured to generate ultraviolet radiation at different wavelengths and dosages. In one embodiment, the set of LED sources can be configured to irradiate the live samples passing through the channels prior to delivery into the containers. In this embodiment, the controller can comprise a plurality of individual controllers each implemented with one of the vaccine delivery channels. In one embodiment, the vaccine delivery channels can comprise pipettes which may contain a fluoropolymer material.

At least one fluorescent sensor can be located about each of the samples and used in conjunction with the ultraviolet radiation source and the controller. In one embodiment, the fluorescent sensor can be configured to obtain fluorescent signals from the live samples after irradiation by the ultraviolet radiation source. The controller can generate a fluorescent signature from the fluorescent signals indicating a presence of growth of the live organisms or inactivation of subsequent growth.

A first aspect of the invention provides a system, comprising: a plurality of containers configured to store a culture of live organisms developed for a vaccine; a stand to support the plurality of containers; an ultraviolet radiation source configured to irradiate the live organisms in the plurality of containers; and a controller configured to control irradiation of the live organisms in the plurality of containers by the ultraviolet radiation source during development of the vaccine, wherein the controller directs the ultraviolet radiation source to perform an inactivation test of the live organisms using ultraviolet radiation irradiated at a plurality of different wavelengths and a plurality of different dosages of ultraviolet radiation, wherein the controller compares results from the inactivation test against results obtained from a recognition test in which samples of the vaccine irradiated at the plurality of different wavelengths and the plurality of different dosages of ultraviolet radiation are evaluated for an immunogenic response to an antigen with an antibody that acts against the antigen, the controller determining an area of acceptable radiation dosages and wavelengths generated from the ultraviolet radiation source that irradiate the live organisms without affecting efficacy in obtaining the immunogenic response to the antigen and safety of the vaccine, wherein the area of acceptable ultraviolet radiation dosages and wavelengths is representative of a difference between an ultraviolet radiation dosage that is required for inactivation and an ultraviolet radiation dosage that fails to obtain the immunogenic response.

A second aspect of the invention provides a method, comprising: placing a culture of live organisms developed for a vaccine in an array of samples; performing an inactivation test of the live organisms using ultraviolet radiation irradiated at a plurality of different wavelengths and a plurality of different dosages of ultraviolet radiation; performing a recognition test on the live organisms after the inactivation test; comparing results from the inactivation test and the recognition test; and determining an area of acceptable radiation dosages and wavelengths that irradiate the live organisms without affecting efficacy and safety of the vaccine, wherein the area of acceptable ultraviolet radiation dosages and wavelengths is representative of a difference between an ultraviolet radiation dosage that is required for inactivation and an ultraviolet radiation dosage that leads to a loss of recognition.

A third aspect of the invention provides a system, comprising: a plurality of containers configured to store a culture of live organisms developed for a vaccine; an ultraviolet radiation source having a plurality of individual LED sources each configured to irradiate the live organisms in the plurality of containers; and a controller configured to control irradiation of the live organisms in the plurality of containers by the ultraviolet radiation source during development of the vaccine, wherein the controller directs the ultraviolet radiation source to perform an inactivation test of the live organisms using ultraviolet radiation irradiated at a plurality of different wavelengths and a plurality of different dosages of ultraviolet radiation, wherein the controller compares results from the inactivation test against results obtained from a recognition test in which samples of the vaccine irradiated at the plurality of different wavelengths and the plurality of different dosages of ultraviolet radiation are evaluated for an immunogenic response to an antigen with an antibody that acts against the antigen, the controller determining an area of acceptable radiation dosages and wavelengths generated from the ultraviolet radiation source that irradiate the live organisms without affecting efficacy in obtaining the immunogenic response to the antigen and safety of the vaccine, wherein the area of acceptable ultraviolet radiation dosages and wavelengths is representative of a difference between an ultraviolet radiation dosage that is required for inactivation and an ultraviolet radiation dosage that fails to obtain the immunogenic response, the controller selecting a wavelength from the area of acceptable radiation dosages and wavelengths that yields a largest dose difference between the dosage that is required for inactivation and the dosage that fails to obtain the immunogenic response, and selecting a dosage of radiation from the area of acceptable radiation dosages at the selected wavelength that is in a range of a dosage that is required for inactivation and a dosage that fails to obtain the immunogenic response.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 12 is a schematic representation of a process flow describing a wavelength-dose immunogenicity (recognition) test that can be implemented with a system for preparing a vaccine according to an embodiment.

FIG. 13 shows an example a of graphical representation derived from a recognition test according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
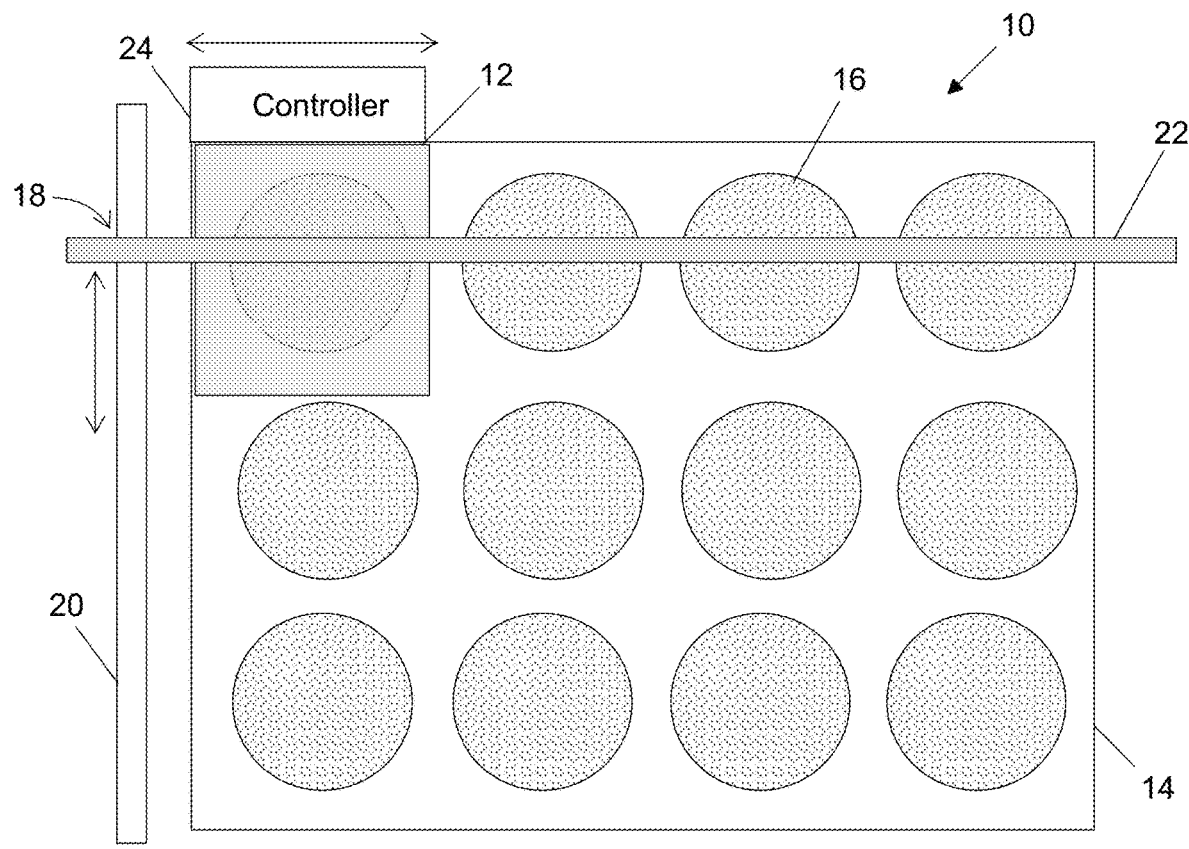
FIG. 1 shows a schematic of a system for preparing a vaccine with an ultraviolet radiation source according to an embodiment.

As indicated above, aspects of the present invention are directed to the inactivation of viruses or bacteria through the use of ultraviolet radiation for the purpose of developing a vaccine that stimulates antibody production that confers immunity to a particular disease. It is believed that the current state of the art in vaccine development and preparation have yet to explore the feasibility of inactivation of viruses and bacteria using ultraviolet radiation from an ultraviolet radiation source, such as for example, a light emitting diode (LED) lamp with multiple wavelengths of ultraviolet light and dosages of ultraviolet radiation. In one embodiment, an ultraviolet radiation source such as a light emitting diode (LED) lamp having individual LED sources each configured to irradiate at specific wavelength selected from a range extending from 250 nm to 360 nm can be used in the inactivation of live samples of biological elements such as for example, infectious agents (e.g., viruses or bacteria).

In other embodiments, the use of the ultraviolet radiation source for inactivation purposes can be combined with other inactivation methods that include but are not limited to, heating inactivation, chemical inactivation (e.g., formaldehyde inactivation, inactivating psoralen, inactivating furocoumarin), partial heating inactivation and partial chemical inactivation. The use of an ultraviolet radiation source alone for the purpose of inactivation of biological elements or in combination with other inactivation modalities enables the vaccine to act as an adjuvant that improves the reaction of a body's immune system to the administered modified antigen entities, and thus, enhances the body's immune response to the antigens.

The use of ultraviolet radiation for the purpose of inactivation of biological elements in the development and preparation of a vaccine according to the various embodiments described herein is suitable for inactivating a wide variety of viruses and bacteria. Examples of bacteria and viruses that can be the subject of the inactivation and vaccine development in the various embodiments can include, but are not limited to, an arbovirus, a dengue virus including dengue-1, dengue-2, dengue-3, dengue-4, and combinations thereof, and the Ebola virus.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 360 nm provides the highest inactivation effectiveness. While susceptibility to ultraviolet radiation varies, exposure to ultraviolet energy in the above range for about 20 to about 34 milliwatt-seconds/$cm^2$ is adequate to inactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

The ultraviolet radiation sources and systems including ultraviolet radiation sources as described herein can include a number of components described below in more detail, some of which may be optional, that facilitate the inactivation of biological elements in the development and preparation of vaccines. The modalities used with the various ultraviolet radiation sources and systems described herein including its respective components can include any now known or later developed approaches that incorporate the concepts of the embodiments described below in more detail.

Referring now to the drawings, FIG. 1 shows a schematic of a system 10 for preparing a vaccine with an ultraviolet radiation source 12 according to an embodiment. As shown in FIG. 1, the system 10 can include a stand 14 to support a plurality of containers 16 that can each store a sample of a vaccine containing a culture of live organisms. The ultraviolet radiation source 12 is configured to irradiate the live organisms in the plurality of containers 16 through the use of a rail device 18 that includes rails 20 and 22 that move the ultraviolet radiation source 12 along the stand in different directions to emit radiation towards each of the containers containing the organisms.

A controller 24 can control the irradiation of the live organisms in the containers 16 by the ultraviolet radiation source 12 during development and preparation of the vaccine. In one embodiment, the controller 24 directs the ultraviolet radiation source 12 to perform an inactivation test of the live organisms using ultraviolet radiation irradiated at a plurality of different wavelengths and a plurality of different dosages of ultraviolet radiation. The controller 24 can compare the results from the inactivation test against results obtained from a recognition test in which samples of the vaccine were irradiated at the plurality of different wavelengths and the plurality of different dosages of ultraviolet radiation, and evaluated for an immunogenic response to an antigen with an antibody that acts against the antigen. Based on this comparison, the controller 24 can determine an area of acceptable radiation dosages and wavelengths generated from the ultraviolet radiation source that can irradiate the live organisms without affecting efficacy in obtaining the immunogenic response to the antigen and safety of the vaccine. In one embodiment, the area of acceptable ultraviolet radiation dosages and wavelengths is representative of a difference between an ultraviolet radiation dosage that is required for inactivation and an ultraviolet radiation dosage that fails to obtain the immunogenic response. Below are further details of the inactivation test, the recognition test and the comparison of the results to ascertain an area of acceptable radiation dosages and wavelengths.

The ultraviolet radiation source 12 can comprise any combination of one or more ultraviolet radiation emitters. Examples of ultraviolet radiation emitters can include, but are not limited to, high intensity ultraviolet lamps (e.g., high intensity mercury lamps), discharge lamps, ultraviolet LEDs, super luminescent LEDs, laser diodes, and/or the like. In one embodiment, the ultraviolet radiation source 12 can include a set of LEDs manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the ultraviolet radiation source 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like.

It is understood that the number of ultraviolet radiation sources 12 illustrated in FIG. 1 and the other various embodiments described herein is only illustrative. Those skilled in the art will appreciate that any number of ultraviolet radiation sources 12 may be utilized to irradiate the samples of organisms in the containers 16. For example, the system 10 can employ only one ultraviolet radiation source 12 or multiple ultraviolet radiation sources 12 can be located along different positions of the stand 14.

Figure 2:
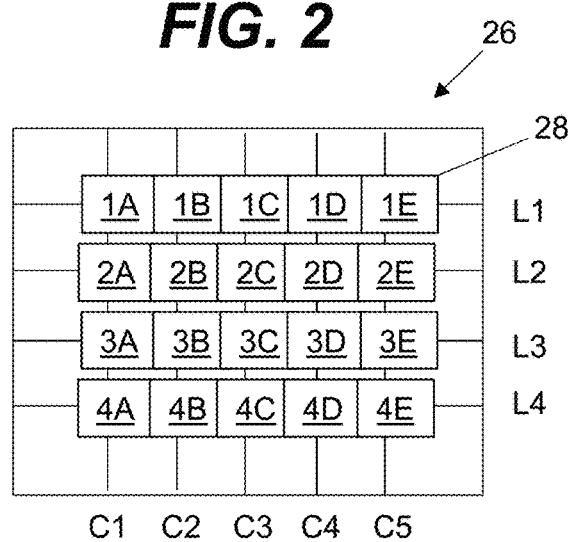
FIG. 2 shows a schematic of an ultraviolet light emitting diode (LED) lamp with individual LED sources that can be used in a system for preparing a vaccine according to an embodiment.

In one embodiment, the ultraviolet radiation source 12 can comprise an ultraviolet LED lamp having a plurality of individual LED sources each configured to irradiate at specific wavelength selected from a range extending from 250 nm to 360 nm. FIG. 2 shows a schematic of an ultraviolet LED lamp 26 with individual LED sources 28 that can be used in a system for preparing a vaccine according to an embodiment. As shown in FIG. 2, the individual LED sources 28 of the ultraviolet LED lamp 26 comprises individual LED sources 1A . . . 4E with each source capable of irradiation at a specific wavelength within the 250 nm to 360 nm range. In one embodiment, the sources can be irradiated at a 270 nm, 280 nm, 290 nm, 300 nm, and/or 310 nm wavelength emission. It is understood that wavelength emission refers to a peak radiation emission with a peak half width being at most 20 nm. In one embodiment, each individual LED source 28 can be controlled with an on/off device switch that can, for example, comprise a transistor. In one embodiment, the individual LED sources 28 can be arranged in a matrix. U.S. patent application Ser. No. 15/283,490 entitled Integrated Flip Chip Device Array, filed 3 Oct. 2016 discusses the use of active matrix technology to arrange individual LED sources and is incorporated herein by reference.

Figure 3:
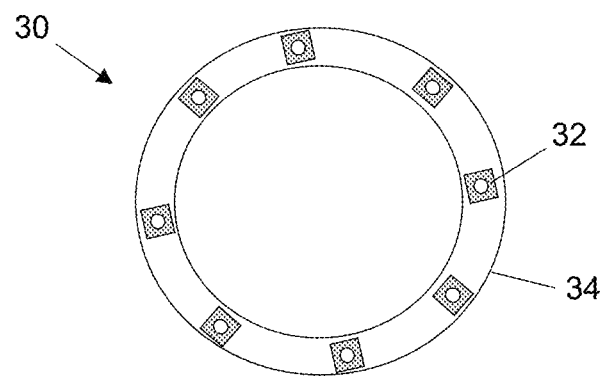
FIG. 3 shows a schematic of an ultraviolet LED lamp with individual LED sources arranged in a ring shape that can be used in a system for preparing a vaccine according to an embodiment.

FIG. 3 shows another embodiment of a type of ultraviolet radiation source that can be used in a system for preparing a vaccine according to an embodiment. In particular, FIG. 3 shows a schematic of an ultraviolet LED lamp 30 with individual LED sources 32 arranged in a ring shape on an ultraviolet radiation source holder 34 that can be used in a system for preparing a vaccine according to an embodiment. Each of the individual LED sources 32 can be arranged and oriented along the holder 34 to emit the ultraviolet radiation towards the containers (not shown in FIG. 3) storing the live samples of the organisms in a manner that obtains a desired coverage of the radiated light that attains inactivation of the organisms. It is understood that a multiple number of different arrangements of the LED sources 32 along the holder 34 that can facilitate inactivation are possible. Furthermore, it is understood that the LED sources 32 can be arranged along the holder 34 to form shapes other than a ring, such as for example, a rectangular shape, and still operate to perform the desired inactivation.

Figure 4:
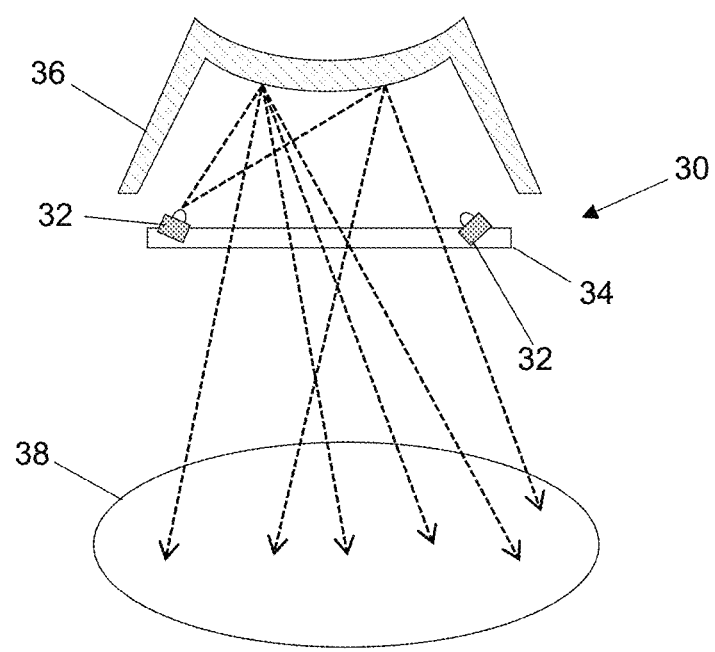
FIG. 4 shows a schematic of an ultraviolet radiation source having individual ultraviolet radiation sources arranged on an ultraviolet radiation source holder and operating in conjunction with diffusive elements that can be implemented with a system for preparing a vaccine according to an embodiment.

FIG. 4 shows a schematic of the ultraviolet LED lamp 30 with the individual LED sources 32 arranged on the ultraviolet radiation source holder 34 as depicted in FIG. 3 operating in conjunction diffusive elements according to an embodiment. The diffusive elements can enable recycling of the ultraviolet radiation generated from the individual LED sources 32. In one embodiment, as shown in FIG. 4, a first diffusive element 36 can be placed over the containers storing the live samples of organisms and a second diffusive element 38 can be placed on the stand underneath the plurality of containers. Note for clarity, the containers and stand are not illustrated in FIG. 4. In the embodiment of FIG. 4, the source holder 34 with the individual LED sources 32 can be located between the first diffusive element 36 and the second diffusive element 38. As shown in FIG. 4, the LED sources 32 can be oriented to direct the ultraviolet radiation towards the first diffusive element 36. The first diffusive element 36 directs the ultraviolet radiation toward the containers placed on the second diffusive element 38 and the stand which can provide a diffusive screen for uniform emission of the ultraviolet radiation. In this manner, the live samples can receive the desired amount of ultraviolet radiation at a selected wavelength and dosage.

In one embodiment, the first diffusive element 36 can comprise a highly diffusively reflective material that ensures that most of the ultraviolet radiation from the LED source 32 is directed towards and through second diffusive element 38. As used herein, a highly diffusively reflective material means a material for which the radiation reflected from the surface is either Lambertian or close to Lambertian. In particular a highly diffusive reflective material can be defined as having at least 50% Lambertian diffusion upon reflection. Examples of a highly diffusively reflective material that is suitable for use as the first diffusive element 36 can include, but is not limited to, a highly ultraviolet reflective expanded polytetrafluoroethylene (ePTFE) membrane (e.g., GORE® Diffuse Reflector Material), PTFE, a diffusively reflective polymer (e.g., TEFLON), or similar material capable of diffusive reflectivity.

In one embodiment, the second diffusive element 38 can be a diffusive screen that comprises a diffusively transparent material. As used herein, a diffusively transparent material means a material for which radiation transmitted through the material has at least partially a Lambertian distribution. In particular, a diffusively transparent material can be defined as having at least 30% Lambertian diffusion upon transmission. Furthermore, a highly diffusively transparent material can be defined as having at least 50% Lambertian diffusion upon transmission. Examples of diffusively transparent materials that are suitable for use as the second diffusive element 36 can include, but are not limited to, fluoropolymer films (e.g., TEFLON films). In one embodiment, the second diffusive element 36 can include a set of layers comprising fluoropolymer films, such as TEFLON films, being diffusively transparent.

In the embodiment depicted in FIG. 4, the source holder 34 can comprise an ultraviolet transparent material. Examples of an ultraviolet transparent material that is suitable for use with the source holder 34 can include, but is not limited to, an ultraviolet transparent fluoropolymer chosen from the group consisting of fluorinated ethylene-propylene (EFEP), ethylene-tetrafluoroethylene (ETFE), Teflon®, and fluorinated ethylene propylene (FEP). In one embodiment, the source holder 34 can include an ultraviolet transparent material such as sapphire, fused silica or the like. In another embodiment, the holder can comprise a plastic or metal.

Figure 5:
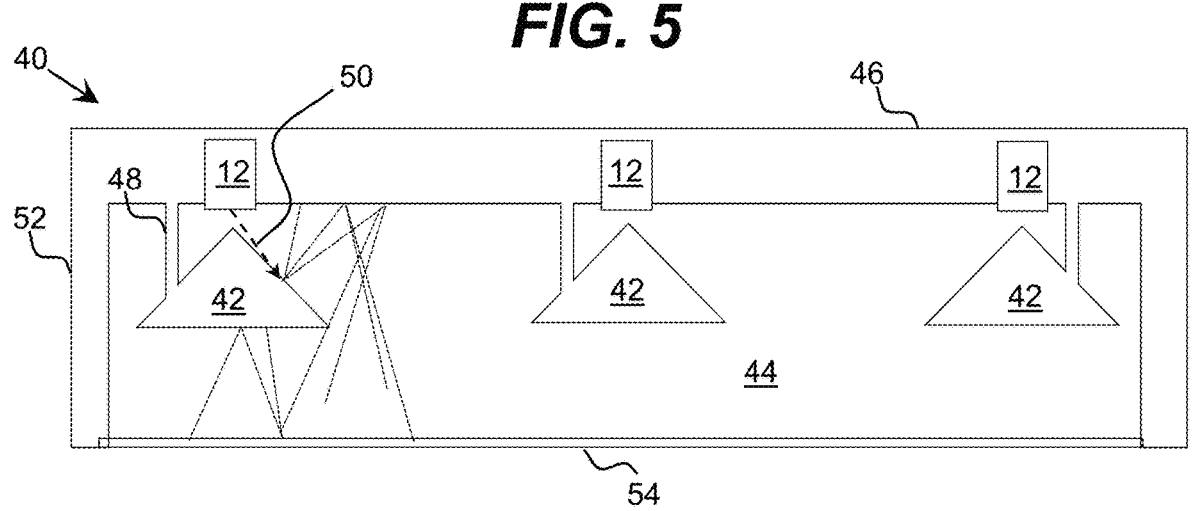
FIG. 5 shows a schematic of a diffuser with mirrors operating in conjunction with ultraviolet radiation sources that can be implemented with a system for preparing a vaccine according to an embodiment.
Figure 6:
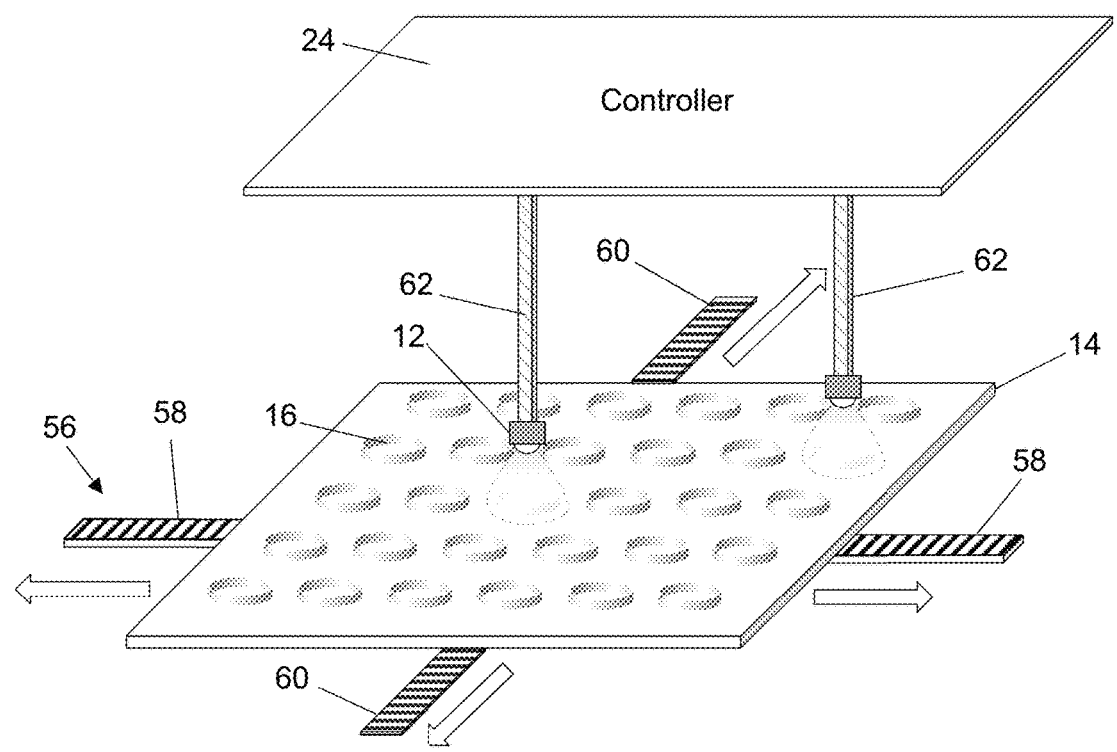
FIG. 6 shows a schematic of a two-dimensional rail system having an x-axis motion rail and a y-axis motion rail operating in conjunction with ultraviolet radiation sources that can be implemented with a system for preparing a vaccine according to an embodiment.

FIG. 5 shows a schematic of a diffuser illuminator 40 with optical elements such as a set of reflecting mirrors 42 operating in conjunction with ultraviolet radiation sources 12 that can be implemented with a system for preparing a vaccine according to an embodiment to ensure diffusive illumination. In FIG. 5, the ultraviolet radiation sources 12 can be positioned on a surface in a reflective cavity 44 that is highly reflective. In one embodiment, the ultraviolet radiation sources 12 can be positioned on a top surface 46 of the cavity 44. In this embodiment, each of mirrors 42 can extend from the top surface 46 of the cavity 44 by a leg 48 and be placed underneath one of the ultraviolet radiation sources 12. Each leg 48 can attach to any portion of a mirror 42.

In this configuration, the set of mirrors 42 can be used to increase scattering of the light generated from the ultraviolet radiation sources by diffusively reflecting and recirculating the ultraviolet radiation. In one embodiment, each of the mirrors 42 can take the form of a cone shape with a vertex that is directed towards an ultraviolet radiation source 12. The vertex of each of the mirrors 42 can be located a predetermined distance from the ultraviolet radiation source 12. The predetermined distance can be on the order of the diameter of the ultraviolet radiation source 12.

The mirrors 42 can comprise a highly diffusive ultraviolet radiation material, such as a highly ultraviolet reflective expanded polytetrafluoroethylene (ePTFE) membrane (e.g., GORE® Diffuse Reflector Product (DRP)), and/or the like. In an embodiment, the mirrors 42 can comprise a fluoropolymer, such as fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), Teflon, and/or the like. In one embodiment, the fluoropolymers can be chosen from the group consisting of EFEP, FEP, PFA, Fluon® LM-ETFE AH or THV, ETFE, PTFE, PFA, FLUON® LM. In one embodiment, these fluoropolymer materials can be incorporated into the ultraviolet radiation sources 12 for light guiding and diffusive scattering. In still another embodiment, the reflecting mirrors 42 can be partially ultraviolet reflecting and partially ultraviolet transparent. For example, the mirrors 42 can comprise an ultraviolet reflective film over an ultraviolet transparent film. In an embodiment, the mirrors 42 can be configured to provide specular reflection and can comprise, for example, polished aluminum, and/or the like. In one embodiment, In operation, an original incident of ultraviolet radiation 50 from the ultraviolet radiation sources 12 can be diffusively reflected by the mirror 42 and then again diffusively reflected by the surfaces of the reflective cavity 44 including the top surface 46, side surfaces 52 and a bottom surface 54. This diffusive ultraviolet radiation can exit the reflective cavity 44 through the bottom surface 54 which can be a partially transparent and partially reflective surface, such as a diffusive film. In this manner, the reflecting mirrors 42 and the high diffusive reflectivity of the surfaces in the reflective cavity 44 distribute and diffusively reflect the ultraviolet radiation from the ultraviolet radiation sources 12 such that the bottom surface 54 of the can have an approximately Lambertian reflectance. In this manner, the diffusive illuminator 40 is capable of delivering relatively uniform radiation over a surface of the vaccine sample, wherein "relatively uniform" radiation entails variations in intensity of no larger than 30% over the surface of the vaccine sample being irradiated. U.S. patent application Ser. No. 14/478,266, entitled “Ultraviolet Diffusive Illumination”, filed on 5 Sep. 2014 provides additional details of a diffuser and is incorporated herein by reference.

As mentioned above with regard to FIG. 1, the system 10 for preparing a vaccine with an ultraviolet radiation source 12 can use a rail device 18 with rails 20 and 22 to move the ultraviolet radiation source along the stand 14 in different directions to emit radiation towards each of the containers 16 containing the organisms. In one embodiment, the rail device 18 with rails 20 and 22 can take the form of a linear motion rail system. In one embodiment, the linear motion rail system can include a first linear motion rail and a second linear motion rail that operate in conjunction to move the ultraviolet radiation source 12 in a predetermined direction with respect to the plurality of containers 16. In one embodiment, the first linear motion rail can be configured to move the ultraviolet radiation source 12 in a horizontal direction over the plurality containers 16, while the second linear motion rail can be configured to move the ultraviolet radiation source in a vertical direction over the plurality containers. In this manner, the ultraviolet radiation source 12 can be allowed to move from one container to another container and deliver the appropriate ultraviolet radiation dose at a selected wavelength of light.

In another embodiment, instead of moving the ultraviolet radiation source 12 over the containers as depicted in FIG. 1, the stand 14 and the containers can be moved with respect to the ultraviolet radiation source. FIG. 6 shows a schematic of a two-dimensional rail system 56 having an x-axis motion rail 58 and a y-axis motion rail 60 which can move the stand 14 in x-directional movements and y-axis directional movements with respect to the ultraviolet source 12. FIG. 6 shows that the ultraviolet radiation source 12 can include two ultraviolet LED lamps that are held over the containers 16 by arm connectors 62 that attach to the controller 24 which can control irradiation of the LED lamps, as well as the movement of the stand 14 over the x-axis motion rail 58 and the y-axis motion rail 60.

Although FIG. 6 shows the use of two ultraviolet LED lamps, it is understood that more or less lamps are within the scope of this embodiment. Regardless of the number of ultraviolet LED lamps that are used, the two-dimensional rail system 56 with the x-axis motion rail 58 and the y-axis motion rail 60 can move the stand 14 in relation to the ultraviolet LED lamps such that each container 16 with live organisms can be irradiated by one of the lamps at the appropriate ultraviolet radiation dose and selected wavelength of light. While illustrative systems are shown in which only the ultraviolet source(s) or the stand is moved, it is understood that embodiments can be configured to move both the ultraviolet source(s) and the stand. For example, an embodiment can be configured to enable movement of the ultraviolet source(s) along one of the x-axis or y-axis and movement of the stand along the other of the x-axis or y-axis.

FIG. 7 shows a schematic of vaccine delivery channels 64 that can operate with a system for preparing a vaccine according to an embodiment. In this embodiment, the vaccine delivery channels 64 can supply the culture of live organisms to containers 16 on the stand 14 after being irradiated at a targeted wavelength and radiation dosage for inactivation purposes by a set of ultraviolet sources 66 arranged along the length of the channels 64. The set of ultraviolet sources 66 in each of the vaccine delivery channels can include an ultraviolet LED lamp with individual LED 68 sources each configured to emit radiation at the target wavelength and dosage. As shown in FIG. 7, each of the vaccine delivery channels 64 can further include a controller 70 that can control the irradiation of ultraviolet sources 68 and the amount, the flow and the duration of the irradiated vaccine through the channel into a container 16 until an appropriate level has been reached. Once the container 16 is filled with the culture to a required level, the controller 70 can terminate the flow of the culture. The stand 14 can then be moved to change the position of containers 16 such that the vaccine delivery channels 64 deliver irradiated amounts of the vaccine to another set of containers.

The operation of filling the containers 16 with portions of the vaccine using the vaccine delivery channels 64 can be described in more detail with regard to the following acts. First, all of the containers 16 in a row in the stand 14 are filled by one of the vaccine delivery channel 64 in accordance with the parameters specified by each channel's individual controller 70. The filling of the containers 16 in the row can be considered finished after all of the containers in the row has been filled to the desired level. The row of containers 16 that was filled is then moved as shown by arrow 72, so that the next row of containers can be filled by the vaccine delivery channels 64.

During this filling process, the flow of the vaccine through the vaccine delivery channels 64 can vary so that different radiational doses of ultraviolet radiation can be attained, which as noted below is useful in ascertaining the effectiveness of the inactivation performed by the channels' set of ultraviolet radiation sources 68. In one embodiment, the flow of the vaccine within the vaccine delivery channels 64 can be laminar.

In one embodiment, the flow speed can change discretely from one container 16 to another to achieve a different dose of radiation. In some instances, both the intensity and the flow rate of the vaccine culture can be changed to achieve an adequate dose of illumination. It is also noted that different radiation doses can be administered to a culture during its flow down a channel due to changes in the flow velocity in the channel (and the flow velocity is varied). After filling up all of the containers on the stand 16, additional containers can be placed on the stand for similar testing. Afterwards, results of the inactivation can be ascertained and used to compare with results taken from a recognition test that evaluates samples of the vaccine at similar irradiation conditions for immunogenic responses. More details of the inactivation test and the recognition test, and comparison of the results are explained below.

In one embodiment, a heater can be used with the vaccine delivery channels 64 as a complement to improve upon the inactivation provided by the ultraviolet radiation source 68 by performing a full or partial heating inactivation. In particular, the heater can perform a full or partial heating inactivation by destroying the organisms through heating.

Figure 7:
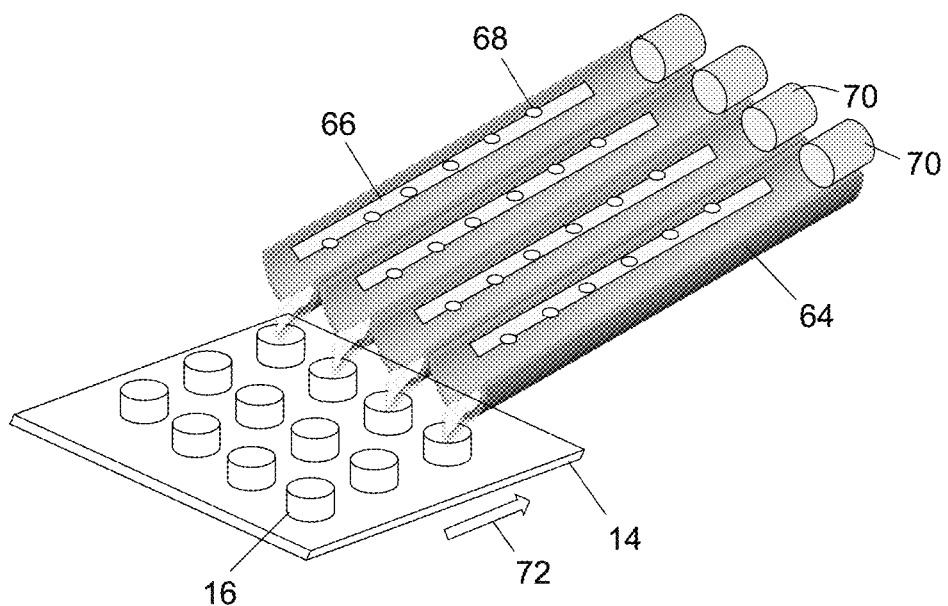
FIG. 7 shows a schematic of vaccine delivery channels that can operate with a system for preparing a vaccine according to an embodiment.
Figure 8:
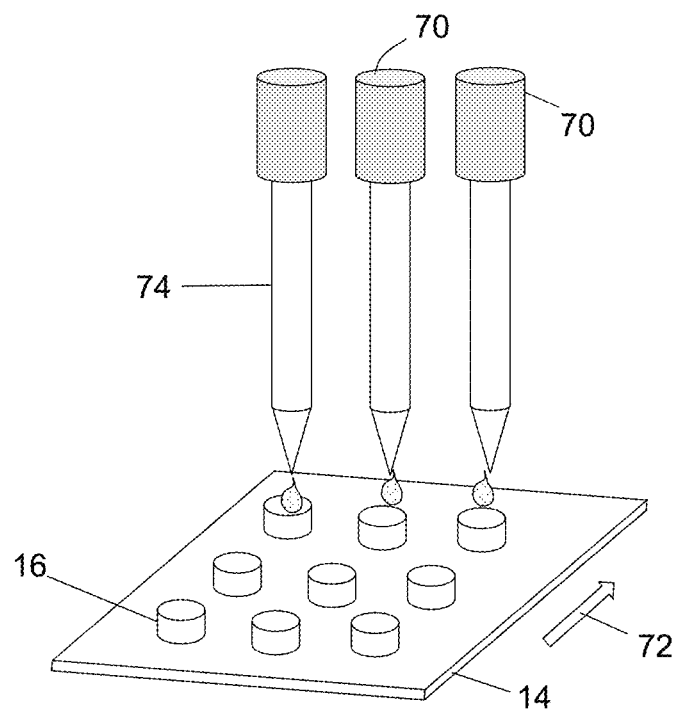
FIG. 8 shows a schematic of alternative vaccine delivery channels that can operate with a system for preparing a vaccine according to an embodiment.

FIG. 8 shows a schematic of alternative vaccine delivery channels 74 that can operate with a system for preparing a vaccine according to an embodiment. In this embodiment, the vaccine delivery channels 74 can take the form of pipettes. Although not illustrated in FIG. 8, each of the pipettes can include an ultraviolet radiation source such as for example, ultraviolet LED lights, that can be placed on the outside of the walls of the pipettes. In one embodiment, the pipettes can include a fluoropolymer material, such as for example, EFEP, PTFE, ETFE, Teflon, and/or the like. In addition, each of the pipettes can include a controller 70 that can control the irradiation by the ultraviolet LED lights and the amount, the flow and the duration of the irradiated vaccine in the pipettes to the containers 16 located on the stand 14. The movement of the stand 14 after the filling of a row of containers with irradiated samples of the vaccine can move in the direction of the arrow 72 to begin delivery of the fluid to the next row of containers 16. Like the embodiment described with respect to FIG. 7, results of the inactivation by the pipettes can be ascertained and used to compare with results taken from a recognition test.

Figure 9:
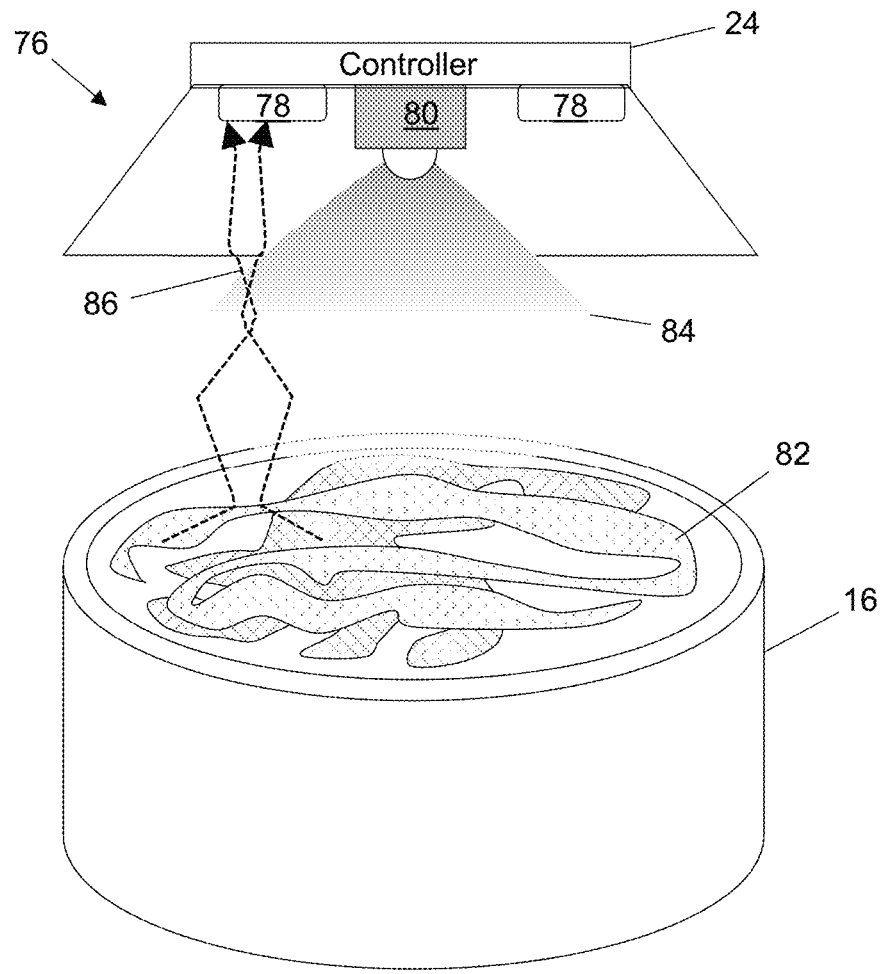
FIG. 9 shows fluorescent sensors operating in conjunction with an ultraviolet radiation source that can operate with a system for preparing a vaccine according to an embodiment.

FIG. 9 shows a system 76 for preparing a vaccine according to an embodiment that uses at least one fluorescent sensor 78 operating in conjunction with an ultraviolet radiation source 80 and a controller 24. In this embodiment, the ultraviolet radiation source 80, which can include any of the aforementioned types, directs a beam 84 of ultraviolet radiation at a sample 82 of live organisms placed on the surface of a container 16. The controller 24 directs the ultraviolet radiation source 80 to supply a targeted amount of radiation, at a certain wavelength, dosage value for a predetermined amount of duration at the sample 82 in order to effectuate inactivation of the sample. The fluorescent sensor(s) 78 can obtain fluorescent signals 86 from the sample 82 that can contain an ultraviolet fluorescent adjuvant, which the controller 24 can use to generate a fluorescent signature.

In one embodiment, controller 24 can use the fluorescent signature to determine if the inactivation performed by the ultraviolet radiation source 80 was carried out successfully. Generally, bacteria and viruses which are present in the sample 82 have a fluorescent signature that is particular to its composition. If the irradiation leads to the growth of bacteria or the virus, then the fluorescent signature can be recognized by the controller 24 and observed as subsequent growth. Similarly, if the controller 24 does not observe that there is a change in the signature, i.e., there is no change from the original signature, then the controller notes that there is a successful inactivation of subsequent growth.

Figure 10:
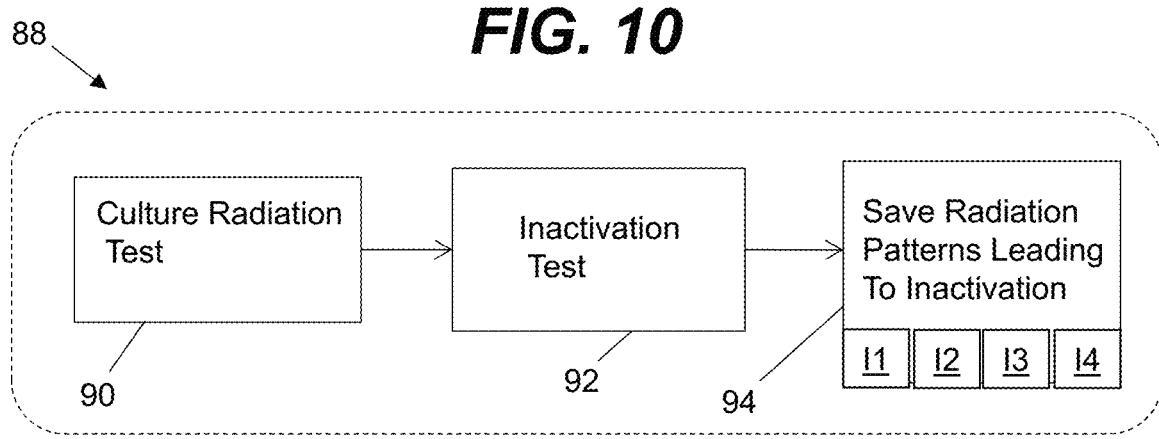
FIG. 10 is schematic representation of a process flow describing a wavelength-dose inactivation test that can be implemented with a system for preparing a vaccine according to an embodiment.

FIG. 10 is schematic representation of a process flow 88 of a wavelength-dose inactivation test that can be implemented with a system for preparing a vaccine according to an embodiment. The first part of the process entails radiating samples of the vaccine at 90. In one embodiment, cultures of live organisms from the vaccine are placed into an appropriate surrounding background in an array of samples. For example, the samples can be placed in containers arranged in an array on a stand. The samples can then be irradiated at specific wavelengths of radiation at varying dosages of radiation. In one embodiment, an ultraviolet LED lamp can be used to irradiate the array of samples at first predetermined wavelength of light, at a first predetermined ultraviolet dosage of radiation.

After the samples have been irradiated, an inactivation test can be performed at 92. In particular, each of the samples in the array are tested for the inactivation of organisms. In one embodiment, each of the samples are examined to determine if there is any organism regrowth, or if not, whether it has been inactivated. For example, the virus growth assay can be used to infer information about microorganism inactivation or attenuation using any solution.

Data from the inactivation test for each of the samples are recorded at 94 such that an analysis can be performed on the data. Data that is recorded can include, but is not limited to, data corresponding to the growth rates of microorganisms. The analysis that can be performed by a computing device such as the aforementioned controller includes determining patterns (e.g., intensities and wavelengths) of radiation that leads to inactivation of the samples. As an example, the process flow 88 shows that the patterns of radiation that lead to inactivation can be labeled and saved as I1, I2, I3 and I4.

These steps of irradiation, performing an inactivation test, recording of data from the inactivation test, and analyzing the data for patterns can be repeated for a set of additional dosages of radiation at that initial wavelength of light. In one embodiment, the set of additional dosages can be selected such that there is at least one dosage of radiation that on average taken over all of the samples produces an inactivation of organisms, and that there is at least one dosage of radiation that on the average does not produce inactivation of organisms. This strategy of selecting dosages enables one to locate the optimal dosage that can lead to inactivation or alteration of microorganism and, at the same time, to result in an appropriate immune response to the microorganisms when the altered/inactivated microorganism is given as a vaccine.

The irradiation, inactivation testing, recording of data from the inactivation testing, analyzing of the inactivation test data, and repetition at the additional set of dosage values at the first predetermined wavelength of light can be repeated through an additional set of ultraviolet wavelength values. This enables selection of a suitable wavelength for irradiation of a particular microorganism. In one embodiment, the additional set of ultraviolet wavelength values that can be evaluated can range from 240 nm to 400 nm.

Figure 11A:
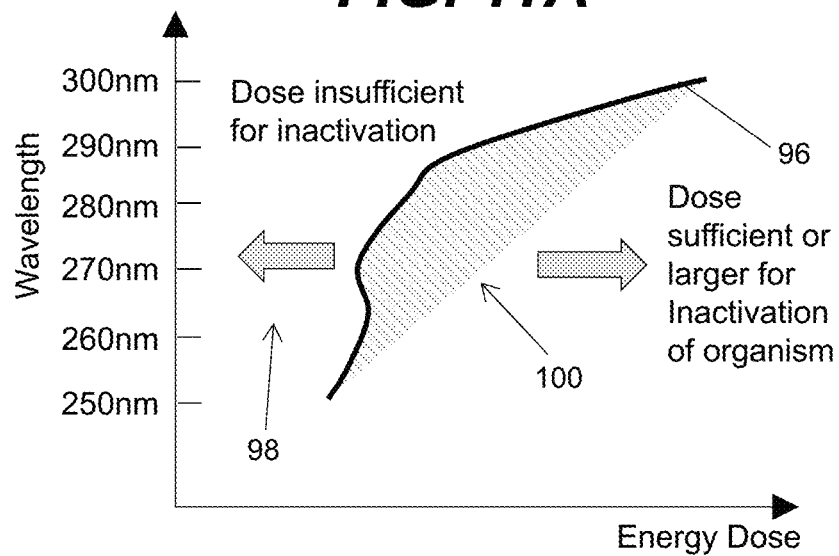
FIGS. 11A-11B show examples of graphical representations derived from a wavelength-dose inactivation test according to an embodiment.
Figure 11B:
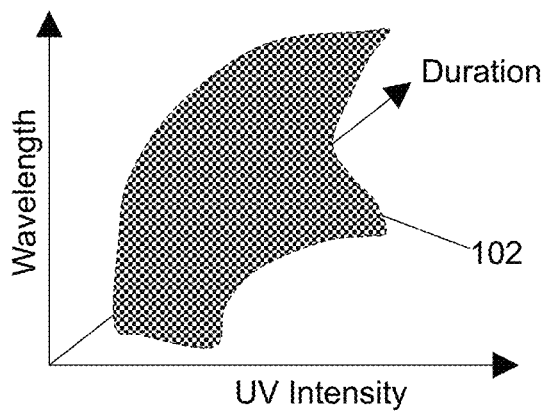

FIGS. 11A-11B show examples of graphical representations illustrating results from a wavelength-dose inactivation test performed in the manner described above according to an embodiment. In particular, the graphical representation illustrated in FIG. 11A depicts an inactivation profile 96 of the vaccine based on the data obtained from the inactivation test for each radiation wavelength at the multiple dosages of radiation values. As used herein, an inactivation profile, which is graphically depicted in FIG. 11A is a function that relates wavelength and energy dose of the ultraviolet light needed for inactivation (attenuation) of the microorganism. As shown in FIG. 11A, region 98 of the graphical representation is indicative of dosages of ultraviolet radiation over a range of wavelengths of light that are insufficient for inactivation of the samples, while region 100 of the graphical representation is indicative of dosages of ultraviolet radiation over the range of wavelengths of light that are sufficient for producing inactivation of the samples. FIG. 11B adds the feature or parameter of time or duration to the representation illustrated in FIG. 11A. In particular, FIG. 11B shows the effect that the variation of time and ultraviolet intensity will have on the inactivation of a culture of the vaccine. More specifically, region 102 represents the range of values on the wavelength, ultraviolet intensity, and time that can be varied to be sufficient to yield inactivation of the culture.

FIG. 12 is schematic representation of a process flow 104 of a wavelength-dose immunogenicity test that can be implemented with a system for preparing a vaccine according to an embodiment. A wavelength-dose immunogenicity test, also known as a recognition test, is generally known in art for vaccines inactivated or attenuated through heating or chemical means. The first part of the process 104 entails radiating samples of the vaccine at 106. In one embodiment, cultures of live organisms from the vaccine are placed into an appropriate surrounding background in an array of samples. For example, the samples can be placed in containers arranged in an array on a stand. Like the inactivation test, the samples for the recognition test can be irradiated at specific wavelengths of radiation at varying dosages of radiation. In one embodiment, an ultraviolet LED lamp can be used to irradiate the array of samples at first predetermined wavelength of light, at a first predetermined ultraviolet dosage of radiation.

After the samples have been irradiated, a recognition test can be performed at 108. In particular, each of the samples in the array are tested for the inactivation of organisms. In one embodiment, each of the samples are examined for recognition (immunogenicity) of an original antigen by an immune system that has developed antibodies after vaccination for each sample. One of a number of recognition testing approaches are suitable for this embodiment. Assay testing or challenge testing are illustrative of a couple of examples of recognition testing that can be deployed. As an example, a challenge test can comprise giving a prepared vaccine to an animal and then evaluating if the vaccine is effective by attempting to infect the animal with a life antigen. An enzyme-linked immunosorbent assay (ELISA) test is an example of assay testing that can be used to determine if a virus or bacteria can be recognized. For example, the ELISA test can be used together with antibodies from an infected animal to test the effectiveness or recognition of the vaccine.

Data showing the response of the immune system delivered from the recognition test for each of the samples are recorded at 110 such that an analysis can be performed on the data. The analysis that can be performed by a computing device such as the aforementioned controller includes determining patterns (e.g., wavelengths, intensities, doses) of radiation that lead to recognition of the samples. As an example, the process flow 100 shows that the patterns of radiation that lead to inactivation can be labeled and saved as R1, R2, R3 and R4.

These steps of irradiation, performing a recognition test, recording data from the recognition test, and analyzing the data for patterns can be repeated for a set of additional dosages of radiation at that initial wavelength of light. In one embodiment, the set of additional dosages can be selected such that there is at least one dosage of radiation that on average taken over all of the samples produces a recognition of organisms and that there is at least one dosage of radiation that on the average does not produce a recognition of organisms.

The irradiation, recognition testing, recording of data from the recognition testing, analyzing of the recognition test data, and repetition thereof at an additional set of dosage values at the first predetermined wavelength of light can be repeated through an additional set of ultraviolet wavelength values. As mentioned above, the additional set of ultraviolet wavelength values that can be evaluated can range from 240 nm to 400 nm.

FIG. 13 shows an example of a graphical representation illustrating results from a recognition test performed in the manner described above according to an embodiment. In particular, the graphical representation illustrated in FIG. 13 depicts a recognition profile 112 of the vaccine based on the data obtained from the recognition test for each radiation wavelength at the multiple dosages of radiation values. As used herein, a recognition profile, which is graphically depicted in FIG. 13 is a function (represented by a curve) that relates wavelength and energy dose of the ultraviolet light needed for loss of recognition of the microorganism by an immune system. As shown in FIG. 13, region 114 of the graphical representation is indicative of dosages of ultraviolet radiation over a range of wavelengths of light that are sufficiently small enough that the organism is recognized by the immune system. That is, the immune system recognizes the original antigen and produces the antibody or antibodies that acts against the antigen. It is understood that without any radiation, the antigen will be recognized by the antibodies of the previously infected organism. Region 116 of the graphical representation is indicative of dosages of ultraviolet radiation over the range of wavelengths of light that are large enough that the immune system does not recognize the antigen, and thus, does not produce the antibody to act against the antigen. It is understood that the amplitude of the dose can significantly change the structure of the bacteria and virus in a sample to affect its recognition.

The results from the recognition test can be compared against the results of the inactivation test for each irradiated wavelength. In one embodiment, a computing unit such as the aforementioned controller can use the data from both tests to calculate the dose required for inactivation and the dose required for loss of recognition. From this information, the difference between the dose required for inactivation and the dose required for loss of recognition for each of the wavelengths can be determined and recorded. The wavelength with the largest dose difference can then be selected and used to choose a radiation dose at the selected wavelength that is in the range of the dose required for inactivation and the dose required for loss of recognition. The selecting of a wavelength with the largest dose difference and choosing of a radiation dose at the selected wavelength that is in the range of the dose required for inactivation and the dose required for loss of recognition can be represented by: [Di+0.8(Dr−Di), Di+0.9(Dr−Di)], wherein Di is the dose required for inactivation and Dr is the dose required for loss of recognition. In this manner, a set of acceptable dosages of radiation values can be determined over a range of wavelengths that can be used to irradiate the live organisms without affecting efficacy in obtaining the immunogenic response to the antigen and safety of the vaccine.

Figure 14:
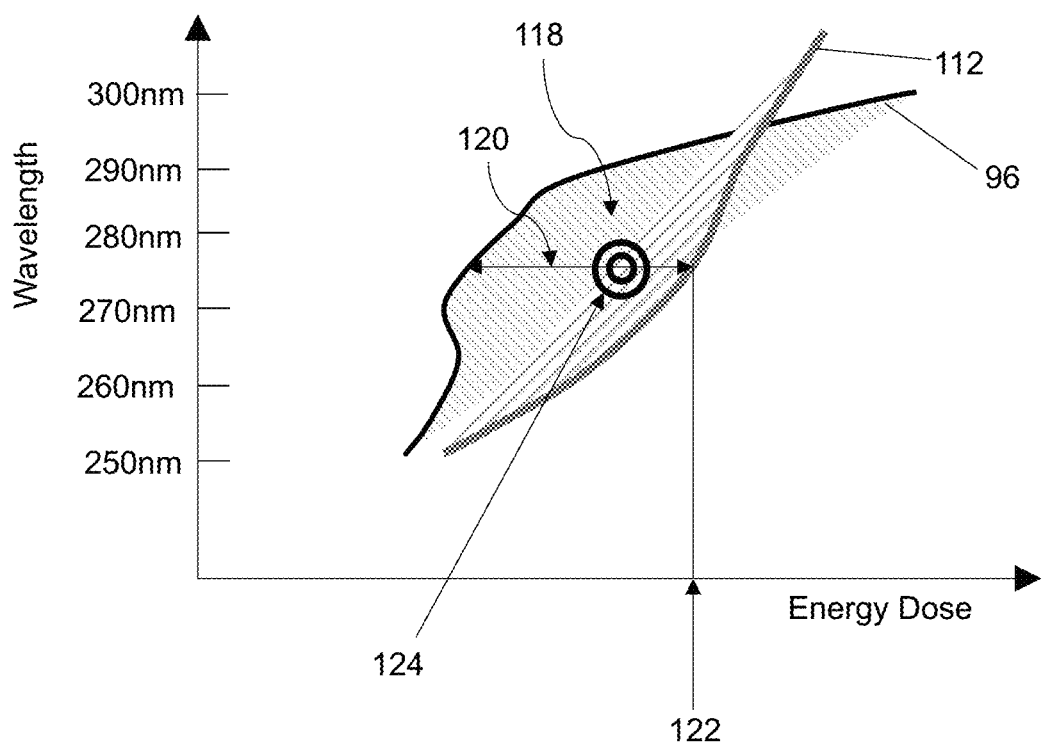
FIG. 14 shows an example of a graph illustrating results derived from both an inactivation test and a recognition test according to an embodiment.

FIG. 14 shows an example of a graph illustrating results obtained from both an inactivation test and a recognition test according to an embodiment. In particular, FIG. 14 shows the comparison of the data associated with the inactivation test 96 depicted in FIG. 11A with the data associated with the recognition test 112 depicted in FIG. 13. Region 118 represents an area of acceptable ultraviolet radiation dosages and wavelengths that can be used to irradiate the live organisms without affecting efficacy in obtaining the immunogenic response to the antigen and safety of the vaccine. More specifically, region 118 is representative of the difference between an ultraviolet radiation dosage that is required for inactivation and an ultraviolet radiation dosage that fails to obtain the immunogenic response. The widest range of the difference an ultraviolet radiation dosage that is required for inactivation and an ultraviolet radiation dosage that fails to obtain the immunogenic response is represented in FIG. 14 by width 120. Point 122 on the recognition profile 112 at the widest difference 120 represents the point of maximum safety, i.e., the largest dose at which recognition can take place. In one embodiment, the process of choosing a wavelength light and radiation dosage value can be selected such that the difference between recognition dose and inactivation dose at a particular wavelength is the largest. Region 124 illustrated in FIG. 14 as a target is indicative of a suggested operational domain for irradiating the vaccine. The target region 124 can be determined by selecting a central point between two curves for each wavelength, and the wavelength can be selected to result in largest separation distance between two curves.

In another embodiment, the inactivation test, recognition test and comparison of their results can involve testing and comparing over various wavelengths of light. For example, in the inactivation test, the step of using an ultraviolet LED lamp to irradiate the array of samples at a first predetermined ultraviolet dosage of radiation can further include irradiating before testing for inactivation of organisms in each of the samples. In one embodiment, after irradiating the samples at a first predetermined wavelength and a first predetermined dosage of radiation, the array of samples can then be irradiated at a second predetermined wavelength at a second predetermined dosage of radiation.

The other steps of the inactivation test can then be performed such as testing for the inactivation of organisms and analyzing the data from the inactivation test can be repeated in the manner described above. For the aspect of the test that involves selecting a set of additional dosage values that lead to inactivation and those that fail to yield inactivation, in this embodiment, a portion of the selection can be based on the first predetermined wavelength and dosage, while another of the selections can be based on the second predetermined wavelength and dosage.

Similarly, the irradiation in the recognition test could involve irradiation of multiple wavelengths and radiation dosage values before testing for recognition. In this embodiment, the irradiation in the recognition test could use the same predetermined wavelengths and dosage values as utilized for the inactivation test. For the embodiment in which the samples are irradiated by a first predetermined wavelength at a first predetermined radiation dosage value and followed by an irradiation at a second predetermined wavelength and a second predetermined dosage, the selection of a set of additional dosage values that lead to recognition of organisms and those that do not can be based on the first predetermined wavelength and dosage, while another of the selections can be based on the second predetermined wavelength and dosage.

Figure 15:
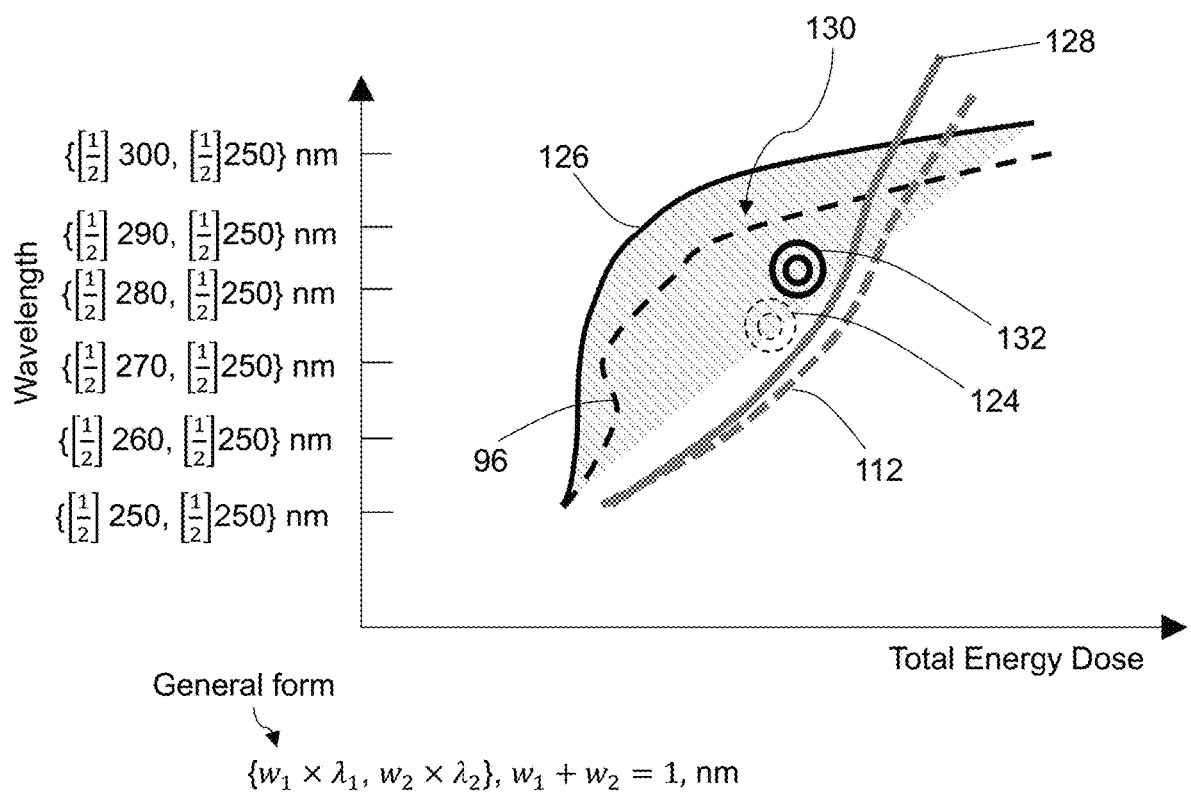
FIG. 15 shows another example of a graph illustrating results derived from both an inactivation test and a recognition test based on the irradiation of the ultraviolet radiation source with several wavelengths according to an embodiment.

FIG. 15 shows an example of a graph illustrating results obtained from both an inactivation test and a recognition test based on the irradiation of samples that involves a first predetermined wavelength and dosage followed by a second predetermined wavelength and dosage before conducting either the respective inactivation testing or recognition testing. FIG. 15 shows the original inactivation profile 96 and the original recognition profile 112, from FIGS. 11A and 13, respectively, in relation to an inactivation profile 126 and a recognition profile 128, respectively, that is based on using a double wavelength radiation and dosage for the inactivation and recognition testing. As shown in FIG. 15, the inactivation profile 126 and the recognition profile 128 are shifted from the inactivation profile 96 and the original recognition profile 112, respectively, which resulted from a particular radiation strategy employed.

The inactivation testing and the recognition testing for this embodiment can be conducted with a number of different pairs of wavelengths as would be appreciated by those skilled in the art. In one embodiment, as illustrated in FIG. 15, at least one of the pairs of wavelengths is 250 nm, while the others can range from 250 nm to 300 nm. For each pair of wavelengths that are used, a dosage of radiation is selected. As illustrated in FIG. 15, the radiation can be undertaken for each wavelength with ½ of the selected dose. It is understood that ½ of the selected dose is used only for illustration and other fractions are possible. For example, the first wavelength can be delivered at ¾ of a dose and the second wavelength can be delivered at ¼ of a dose. It is understood that the pairs of wavelengths used in FIG. 15 are only illustrative and not meant to be limiting as it is clear that other pairs can be used and that the dose duration for each wavelength within the pair can be adjusted as desired.

One alternative embodiment to the various ones described above can include using other inactivation methods as a complement to the inactivation by the use of ultraviolet radiation. These other inactivation methods can include but are not limited to, heating inactivation, chemical inactivation (e.g., formaldehyde inactivation, inactivating psoralen, inactivating furocoumarin), partial heating inactivation and partial chemical inactivation. In one embodiment, samples of the vaccine can be exposed to an inactivating psoralen, wherein the psoralen is selected from the group consisting of 4'-Aminomethyltrioxalen hydrochloride (AMT), 8-Methoxypsoralen (8-MOP), 4, 5', 8-Trimethylpsoralen (TMP) and combinations thereof. In one embodiment, the inactivating psoralen can be added to a medium containing live organisms from the vaccine. In one embodiment, the psoralen can be introduced to the medium in 1-4 additions. In one embodiment, the concentration of the psoralen can be 5-25 μg/ml. In one embodiment, the use of the inactivating psoralen can be administered prior to performing any of the aforementioned steps associated with the inactivation testing and recognition testing.

Another alternative embodiment can include using a mixer to mix the vaccine samples before irradiation of the samples with ultraviolet radiation. In one embodiment, a mixer can rotate the vaccine samples around an axis normal to the illumination surface of mixing. This ensures that all of the parts of vaccine samples obtain sufficient radiation dosages. In another embodiment, the mixer can include a mixing spinning element within the containers that are used to accommodate the vaccine samples.

In yet another alternative embodiment, the irradiation of the samples of the vaccine for both the inactivation testing and the recognition testing can be performed in the substantial absence of oxygen and other oxidizing species. Irradiating the samples in the absence of oxygen and other oxidizing species may be beneficial in that no chemical oxidation is used to affect the vaccine.

Figure 16:
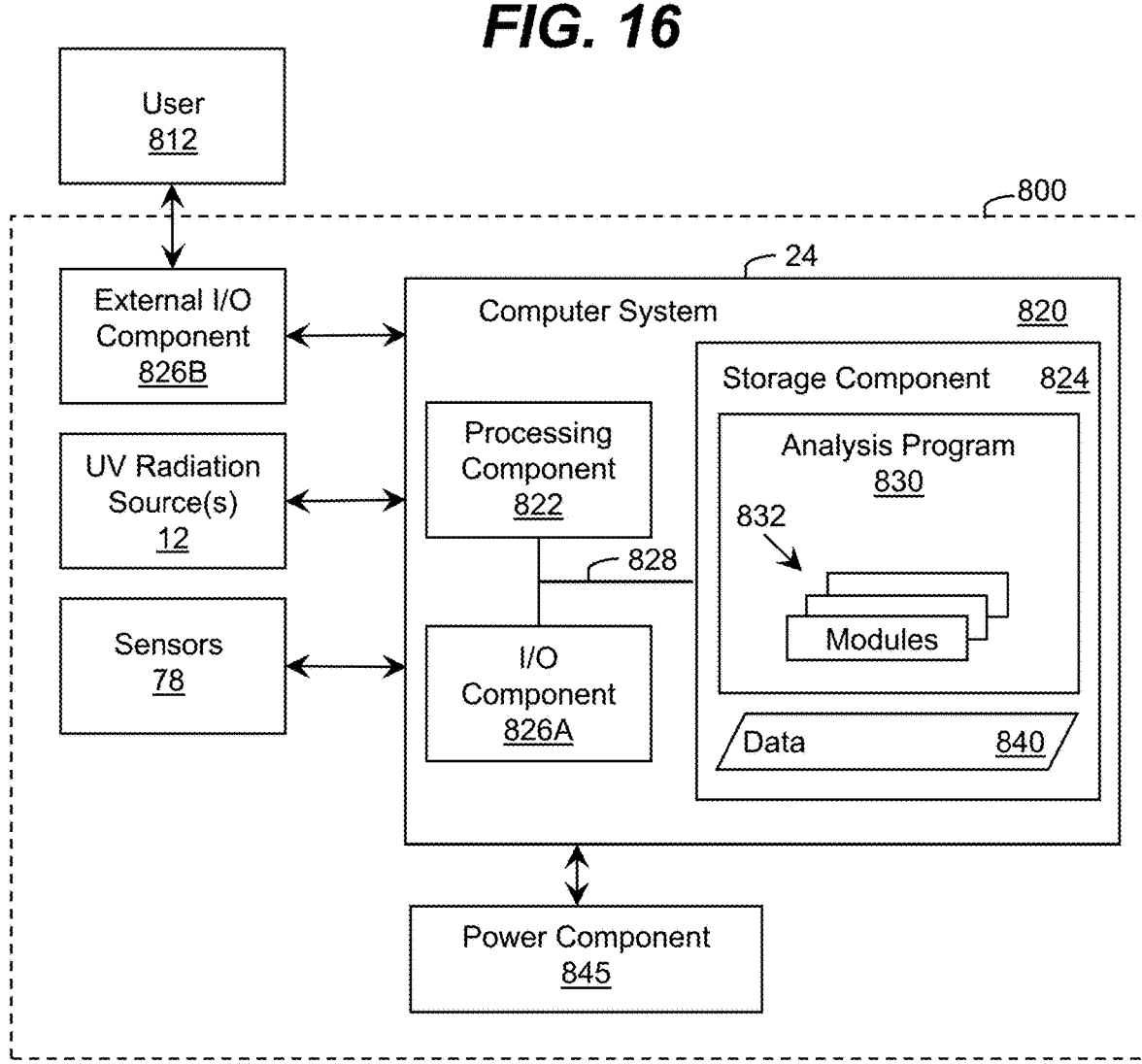
FIG. 16 shows a schematic block diagram representative of an overall processing architecture of a system for preparing a vaccine with an ultraviolet radiation source according to an embodiment.

Referring now to FIG. 16, there is a schematic block diagram representative of an overall processing architecture of a system 800 for preparing a vaccine with an ultraviolet radiation source 12 for effectuating an inactivation test, a recognition test and comparison of results to find an acceptable range of wavelengths and dosages that can be used to irradiate the live organisms in a vaccine without affecting its efficacy. In this embodiment, the architecture 800 is shown including the ultraviolet radiation sources 12 (UV radiation source(s)) and the sensors 78 (e.g., fluorescence sensors) for the purposes of illustrating the interaction of all of the components that can be used to provide a system for preparing a vaccine.

As depicted in FIG. 16 and described herein, the system 800 can include a controller 24. In one embodiment, the controller 24 can be implemented as a computer system 820 including an analysis program 830, which makes the computer system 820 operable to manage the ultraviolet radiation sources 12 and the sensors 78 in the manner described herein. In particular, the analysis program 830 can enable the computer system 820 to operate the ultraviolet radiation sources 12 to generate and direct ultraviolet radiation towards the samples of vaccine and process data from the testing which is stored as data 840. The computer system 820 can individually control each ultraviolet radiation source 12 and sensor 78 and/or control two or more of the ultraviolet radiation sources and the sensors as a group. Furthermore, the ultraviolet radiation sources 12 can emit ultraviolet radiation of substantially the same wavelength or of multiple distinct wavelengths.

In an embodiment, during an initial period of operation, the computer system 820 can acquire data from at least one of the sensors 78 regarding one or more attributes of the device and generate data 840 for further processing. The data 840 can include information pertaining to the results from the inactivation testing and the recognition testing as well the comparison of the data. The computer system 820 can use the data 840 to control one or more aspects of the ultraviolet radiation generated by the ultraviolet radiation source(s) 12 during inactivation and recognition testing.

Furthermore, one or more aspects of the operation of the ultraviolet radiation sources 12 can be controlled or adjusted by a user 812 via an external interface I/O component 826B. The external interface I/O component 826B can be used to allow the user 812 to selectively turn on/off the ultraviolet radiation sources 12. However, it is understood that, in order to turn on the ultraviolet radiation sources 12, the computer system 820 can first determine that a device has been securely placed within a housing, receptacle, container, or the like (e.g., via data acquired by one or more sensors 78).

The external interface I/O component 826B can include, for example, a touch screen that can selectively display user interface controls, such as control dials, which can enable the user 812 to adjust one or more of: an intensity, and/or other operational properties of the set of ultraviolet radiation sources 12 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation sources 12. The external interface I/O component 826B also can include any combination of various output devices (e.g., an LED, a visual display), which can be operated by the computer system 820 to provide status information for use by the user 812. For example, the external interface I/O component 826B can include one or more LEDs for emitting a visual light for the user 812, e.g., to indicate a status of the irradiation of the samples. In an embodiment, the external interface I/O component 826B can include a speaker for providing an alarm (e.g., an auditory signal), e.g., for signaling that ultraviolet radiation is being generated or that an irradiation has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 16 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
   a plurality of containers configured to store a culture of live organisms developed for a vaccine;
   a stand to support the plurality of containers;
   an ultraviolet radiation source configured to irradiate the live organisms in the plurality of containers; and
   a controller configured to direct the ultraviolet radiation source to irradiate the live organisms in the plurality of containers with a wavelength and radiation dosage that is within an acceptable range of wavelengths and radiation dosages that does not affect efficacy and safety of the vaccine, wherein the controller obtains a collection of results from an inactivation test performed on a first set of test samples of the vaccine in which cultures of the live organisms developed for the vaccine were irradiated with ultraviolet radiation at a plurality of different wavelengths and a plurality of different dosages for each wavelength, wherein the controller obtains a collection of results from a recognition test in which a second set of test samples of the vaccine containing the cultures of the live organisms were irradiated with ultraviolet radiation at the plurality of different wavelengths and the plurality of different dosages for each wavelength, of which each test sample of the second set was administered to one of a number different recipients, wherein the controller compares results from the inactivation test against results from the recognition test, wherein the controller determines the acceptable range of wavelengths and radiation dosages based on the comparison, wherein the acceptable range of wavelengths and radiation dosages is representative of a difference between an ultraviolet radiation dosage that is required for inactivation of the live organisms and an ultraviolet radiation dosage that fails to obtain an immunogenic response to an original antigen that is associated with the live organisms.

2. The system of claim 1, wherein the ultraviolet radiation source comprises an ultraviolet light emitting display (LED) lamp having a plurality of individual LED sources each configured to irradiate at specific wavelength selected from a range extending from 250 nm to 360 nm.

3. The system of claim 2, wherein the plurality of individual LED sources in the ultraviolet LED lamp are arranged in a matrix.

4. The system of claim 2, further comprising a first diffusive element placed over the plurality of containers and a second diffusive element placed on the stand underneath the plurality of containers, and wherein the ultraviolet LED lamp comprises an LED source holder located between the first diffusive element and the second diffusive element that is configured to retain the plurality of individual LED sources, wherein the plurality of individual LED sources are oriented on the LED source holder to direct ultraviolet radiation towards the first diffusive element, wherein the first diffusive element directs the ultraviolet radiation toward the plurality of containers placed on the second diffusive element and the stand.

5. The system of claim 4, wherein the LED source holder comprises an ultraviolet transparent material, and wherein the LED source holder comprises a ring shape.

6. The system of claim 4, wherein the first diffusive element comprises a highly diffusively reflective material, and the second diffusive element comprises a diffusively transparent material.

7. The system of claim 2, further comprising a plurality of optical elements, each optical element operatively coupled to one of the LED sources, wherein each of the LED sources and corresponding optical elements are configured to direct ultraviolet radiation to the plurality of containers.

8. The system of claim 1, further comprising a first linear motion rail and a second linear motion rail that operate in conjunction to move the ultraviolet radiation source in a predetermined direction with respect to the plurality of containers, wherein the first linear motion rail is configured to move the ultraviolet radiation source in a horizontal direction over the plurality containers and the second linear motion rail is configured to move the ultraviolet radiation source in a vertical direction over the plurality containers.

9. The system of claim 1, wherein the stand comprises a two-dimensional rail system having an x-axis motion rail and a y-axis motion rail that operate in conjunction to move the stand in two-dimensional movements that include x-axis directional movements and y-axis directional movements with respect to the ultraviolet radiation source.

10. The system of claim 2, further comprising a plurality of vaccine delivery channels each configured to deliver a predetermined amount of vaccine to one of the plurality of containers, wherein each vaccine delivery channel comprises a set of the LED sources that are configured to generate ultraviolet radiation at the plurality of different wavelengths and the plurality of different dosages, wherein the set of LED sources are configured to irradiate the live organisms prior to delivery into the containers, and wherein the controller comprises a plurality of individual controllers each implemented with one of the vaccine delivery channels.

11. The system of claim 10, wherein the plurality of vaccine delivery channels comprises pipettes.

12. The system of claim 1, further comprising at least one fluorescent sensor located about each of the plurality of containers, the fluorescent sensor configured to obtain fluorescent signals from each container having live organisms stored therein after irradiation by the ultraviolet radiation source, the controller generating a fluorescent signature from the fluorescent signals indicating a presence of growth of the live organisms or inactivation of subsequent growth.

13. A system, comprising:

a plurality of containers configured to store a culture of live organisms developed for a vaccine;

an ultraviolet radiation source having a plurality of individual LED sources each configured to irradiate the live organisms in the plurality of containers; and a controller configured to direct the ultraviolet radiation source to irradiate the live organisms in the plurality of containers with a wavelength and radiation dosage that is within an acceptable range of wavelengths and radiation dosages that does not affect efficacy and safety of the vaccine, wherein the controller obtains a collection of results from an inactivation test performed on a first set of test samples of the vaccine in which cultures of the live organisms developed for the vaccine were irradiated with ultraviolet radiation at a plurality of different wavelengths and a plurality of different dosages of ultraviolet radiation for each wavelength, wherein the controller obtains a collection of results from a recognition test in which a second set of test samples of the vaccine containing the cultures of the live organisms were irradiated with ultraviolet radiation at the plurality of different wavelengths and the plurality of different dosages for each wavelength, of which each test sample of the second set was administered to one of a number of different recipients, wherein the controller compares results from the inactivation test against results from the recognition test, wherein the controller determines the acceptable range of wavelengths and radiation dosages based on the comparison, wherein the acceptable range of wavelengths and radiation dosages is representative of a difference between an ultraviolet radiation dosage that is required for inactivation of the live organisms and an ultraviolet radiation dosage that fails to obtain an immunogenic response to an original antigen that is associated with the live organisms, wherein the controller selects a wavelength from the acceptable range of wavelengths and radiation dosages that yields a largest dose difference between the dosage that is required for inactivation and the dosage that fails to obtain the immunogenic response, and wherein the controller selects a dosage of radiation from the acceptable range of radiation dosages at the selected wavelength that is in a range of a dosage that is required for inactivation and a dosage that fails to obtain the immunogenic response.

14. A system, comprising:

a plurality of containers configured to store a culture of live organisms corresponding to an infectious agent that is used in a vaccine;

an ultraviolet radiation source configured to irradiate the live organisms in the plurality of containers during preparation of the vaccine; and a controller configured to determine an area of acceptable radiation dosages and wavelengths that the ultraviolet radiation source can irradiate the live organisms during the preparation of the vaccine without affecting efficacy and safety of the vaccine, wherein the controller obtains a collection of results from an inactivation test performed on a first set of test samples of the vaccine in which cultures of the live organisms developed for the vaccine were irradiated with ultraviolet radiation at a plurality of different wavelengths and a plurality of different dosages for each wavelength, the results from the inactivation test for each wavelength and accompanying dosage including an indication of regrowth of the live organisms, an indication of inactivation of the live organisms, or an attenuation of the live organisms, wherein the controller determines patterns of wavelengths and dosages of the ultraviolet radiation that lead to inactivation of the live organisms in the first set of test samples, wherein the controller obtains a collection of results from a recognition test in which a second set of test samples of the vaccine containing the cultures of the live organisms were irradiated with ultraviolet radiation at the plurality of different wavelengths and the plurality of different dosages for each wavelength, of which each of the second set of test samples was administered to one of a number of recipients, the results from the recognition test for each wavelength and accompanying dosage administered to a recipient including an indication of whether the recipient developed antibodies to an original antigen associated with the infectious agent, wherein the controller determines patterns of wavelengths and dosages of the ultraviolet radiation in the second set of test samples administered to the recipients that lead to a recognition of the original antigen, wherein the controller compares the patterns ascertained from the results of the inactivation test against the patterns ascertained from the results of the recognition test, wherein the controller determines the area of acceptable radiation dosages and wavelengths based on the comparison, wherein the area of acceptable ultraviolet radiation dosages and wavelengths is representative of a difference between an ultraviolet radiation dosage that is required for inactivation of the original antigen and an ultraviolet radiation dosage that fails to obtain an immunogenic response to the original antigen.

15. The system of claim 14, wherein the controller generates an inactivation profile from the determined patterns of wavelengths and dosages of the ultraviolet radiation that lead to inactivation of the live organisms in the first set of test samples, the inactivation profile relating wavelengths and dosages of ultraviolet radiation to inactivation of the live organisms, wherein the inactivation profile delineates a first range of wavelengths and dosages of ultraviolet radiation that are sufficient for inactivation of the live organisms, and a second range of wavelengths and dosages of ultraviolet radiation that are insufficient for inactivation of the live organisms.

16. The system of claim 14, wherein the controller generates an inactivation profile from the determined patterns of wavelengths and dosages of the ultraviolet radiation that lead to inactivation of the live organisms in the first set of test samples, the inactivation profile relating wavelengths, intensity, and duration of ultraviolet radiation to inactivation of the live organisms, wherein the inactivation profile represents a variable range of values on the wavelength, ultraviolet intensity, and duration that are sufficient to yield inactivation of the live organisms.

17. The system of claim 14, wherein the controller generates a recognition profile from the determined patterns of wavelengths and dosages of the ultraviolet radiation that lead to recognition of the original antigen, the recognition profile relating wavelengths and dosages of ultraviolet radiation to recognition of the original antigen, wherein the recognition profile delineates a first range of wavelengths and dosages of ultraviolet radiation that are sufficiently small for recognition of the original antigen, and a second range of wavelengths and dosages of ultraviolet radiation that are insufficient for recognition of the original antigen.

18. The system of claim 14, wherein the controller determines an ultraviolet radiation dosage range required for inactivation of the original antigen and an ultraviolet radiation dosage range required for loss of recognition of the original antigen based on the comparison of the patterns from the results of the inactivation test and the recognition test.

19. The system of claim 18, wherein the controller selects the wavelength with the largest dose difference and a dosage at the selected wavelength that is included in both the range of the dosage required for inactivation and the dosage required for loss of recognition.

20. The system of claim 19, wherein the selected wavelength is selected according to:

$$[Di+0.8(Dr-Di), Di+0.9(Dr-Di)], \text{wherein}$$

Di is the dose required for inactivation and Dr is the dose required for loss of recognition.

* * * * *